(12) United States Patent
Maywald et al.

(10) Patent No.: US 7,253,323 B2
(45) Date of Patent: Aug. 7, 2007

(54) METHOD FOR THE PRODUCTION OF BENZOPHENONES

(75) Inventors: Volker Maywald, Ludwigshafen (DE); Nico Hoffmann, Frankenthal (DE); Michael Keil, Freinsheim (DE); Uwe Josef Vogelbacher, Ludwigshafen (DE); Jan Hendrik Wevers, Hohen-Suelzen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/535,710

(22) PCT Filed: Dec. 1, 2003

(86) PCT No.: PCT/EP03/13483

§ 371 (c)(1),
(2), (4) Date: May 20, 2005

(87) PCT Pub. No.: WO2004/054953

PCT Pub. Date: Jul. 1, 2004

(65) Prior Publication Data

US 2006/0009659 A1    Jan. 12, 2006

(30) Foreign Application Priority Data

Dec. 13, 2002  (DE)  ................. 102 58 669

(51) Int. Cl.
   *C07C 45/00*  (2006.01)
(52) U.S. Cl. .................. 568/315; 568/316; 568/332
(58) Field of Classification Search .............. None
See application file for complete search history.

(56) References Cited

U.S. PATENT DOCUMENTS

| 5,210,313 | A | * | 5/1993 | Wang et al. | ........ | 568/323 |
| 5,476,970 | A | * | 12/1995 | Rains et al. | ........ | 568/323 |
| 5,945,567 | A | * | 8/1999 | Curtze et al. | ........ | 568/333 |
| 6,576,595 | B1 | * | 6/2003 | Rose et al. | ........ | 504/292 |

FOREIGN PATENT DOCUMENTS

| EP | 0 897 904 A1 | 2/1999 |
| EP | 1 295 877 A1 | 3/2003 |
| WO | WO-01/51440 A1 | 7/2001 |

\* cited by examiner

*Primary Examiner*—Sikarl A. Witherspoon
(74) *Attorney, Agent, or Firm*—Birch, Stewart, Kolasch & Birch, LLP

(57) ABSTRACT

A process for preparing benzophenones of the formula I,

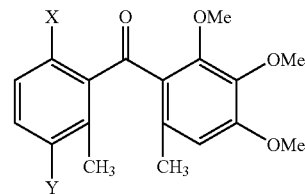

where X may be chlorine, hydroxyl, methoxy or $C_1$-$C_6$-alkylcarbonyloxy, and Y may be chlorine or bromine, by reacting an acid chloride of the formula II

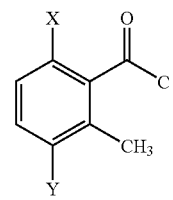

where X and Y are as defined above with 3,4,5-trimethoxy-toluene, which comprises carrying out the reaction in the presence of
  a) an aromatic hydrocarbon as a diluent and
  b) from 0.01 to 0.2 mol % of an iron catalyst, based on the acid chloride,
  c) at a temperature between 60° C. and the boiling point of the particular diluent.

13 Claims, No Drawings

METHOD FOR THE PRODUCTION OF BENZOPHENONES

A process for preparing benzophenones of the formula I,

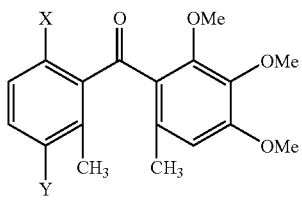

where X may be chlorine, hydroxyl, methoxy or $C_1$-$C_6$-alkylcarbonyloxy, and Y may be chlorine or bromine, by reacting an acid chloride of the formula II

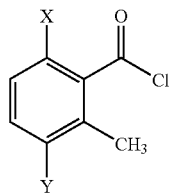

where X and Y are as defined above with 3,4,5-trimethoxytoluene, which comprises carrying out the reaction in the presence of
- a) an aromatic hydrocarbon as a diluent and
- b) from 0.01 to 0.2 mol % of an iron catalyst, based on the acid chloride,
- c) at a temperature between 60° C. and the boiling point of the particular diluent.

The benzophenones of the formula I are disclosed by EP-A 897 904. In this case, the Friedel-Crafts acylation is carried out using stoichiometric amounts of aluminum chloride or phosphorus pentoxide. The diluents used were low boilers such as dichloromethane or benzene. The technical realization of this procedure leads to numerous problems. Particular disadvantages are the aqueous workup and the inevitable occurrence of large amounts of aluminum- or phosphorus-containing wastewater.

WO 01/51440 describes a process for preparing benzophenones I which works in the presence of iron(III) chloride and considerable amounts of graphite. The diluent used is 1,2-dichloroethane. The yield of isolated benzophenone is only approx. 72%. The removal of the graphite also entails an additional filtration step.

It is an object of the present invention to provide an economically viable and selective process for preparing the benzophenones I, which works with catalytic amounts of a Friedel-Crafts catalyst and at the same time delivers high space-time yields.

It has now been found that, surprisingly, the disadvantages present in the prior art can be avoided when the reaction is carried out in the presence of
- a) an aromatic hydrocarbon and
- b) from 0.01 to 0.2 mol % of an iron catalyst, based on the acid chloride,
- c) at a temperature between 60° C. and the boiling point of the particular diluent.

The iron catalyst used is generally finely ground iron powder or iron(III) salts. Preference is given to iron(III) oxide and particular preference to iron(III) chloride.

Useful diluents are high-boiling aromatic hydrocarbons which are inert under the reaction conditions, for example chlorobenzene, benzotrifluoride and nitrobenzene. Particular preference is given to halogenated aromatic hydrocarbons and especially to chlorobenzene.

The use of a relatively high-boiling diluent also has the advantage that the hydrochloric acid forming in the reaction can be removed using an inert gas stream which is preferably passed through the reaction mixture, without resulting in significant diluent losses. It is evident from the preparative examples that the reaction times can be drastically reduced by the inert gas stripping. This allows reaction times of less than 10 hours to be realized even with very low catalyst amounts, for example less than 0.1 mol %, without having to accept relatively large yield losses. Useful inert gases are noble gases such as argon, air and preferably nitrogen. The inert gas stream is preferably passed through the reaction mixture. It is advantageous, for example, to achieve a very fine distribution of the gas particles in the reaction mixture. This can be effected, for example, by means of a jet or of a sparging ring, and these means are advantageously mounted below the stirrer. The amount of gas passed through the reaction mixture depends in particular on the batch size. Up to 5 l/h of inert gas are introduced per mole of acid chloride.

The use of the diluent according to the invention also has the advantage that the Friedel-Crafts acylation can be carried out at relatively high temperatures, which again allow the reaction times to be reduced. In general, operation is effected within the temperature range of from 60° C. to the boiling point of the diluent, preferably within the temperature range of from 80 to 150° C.

The iron catalyst is used in a molar ratio of from 0.01 to 0.2 mol %, based on the acid chloride. Preference is given to using from 0.03 to 0.1 mol % of the catalyst.

The 3,4,5-trimethoxytoluene is also generally used in a molar ratio of from 1 to 3, based on the acid chloride. Preference is given to using a slight excess of from 1.05 to 1.4 molar equivalents of 3,4,5-trimethoxytoluene.

In a preferred embodiment of the process, the 3,4,5-trimethoxytoluene is initially charged, optionally in the diluent, and the iron catalyst and the acid chloride are metered in, optionally in the diluent, within from 0.5 to 20 hours, preferably from 4 to 6 hours, depending on the selected reaction temperature. The iron catalyst is preferably metered in dissolved in the acid chloride.

The reverse procedure (metering in of 3,4,5-trimethoxytoluene) as a one-pot variant has apparatus advantages when acid chloride has already been prepared in the same reaction vessel. As is evident from table 1, this procedure leads to a somewhat lower selectivity and yield in an otherwise identical procedure.

On completion of metering in, the reaction mixture is generally stirred for up to a further 20 hours and preferably from 2 to 4 hours. The continued stirring time can generally be shortened when the solvent and any excess 3,4,5-trimethoxytoluene are distillatively removed at the end of the Friedel-Crafts acylation. The distillation can be begun when only a partial conversion has been achieved. The distillation time can be used to complete the conversion.

The distillative removal of the diluent is the preferred workup variant. The distillation residue remaining in the reaction vessel is a melt of the desired benzophenone which can be crystallized using a $C_1$-$C_6$-alcohol, preferably methanol. It may often be advantageous to add small amounts of water to the alcohol, in order to completely dissolve the iron salts.

The process according to the invention is suitable in particular for preparing 5-bromo-2',6-dimethyl-2,4',5',6'-tetramethoxy-benzophenone. The process according to the invention can also be used to prepare, for example, 2,5-dichloro-2',6-dimethyl-4',5',6'-trimethoxybenzophenone, 5-chloro-2',6-dimethyl-2-hydroxy-4',5',6'-trimethoxybenzophenone or 5-bromo-2',6-dimethyl-2-hydroxy-4',5',6'-trimethoxybenzophenone. In the case of the two latter compounds, it may be advisable to protect the free hydroxyl group in the 2-position in the form of a $C_1$-$C_6$-alkylcarbonyloxy group and to detach it again after the end of the Friedel-Crafts acylation.

The process according to the invention has the advantage that exclusively the desired triclinic modification is obtained. In the processes known hitherto, mixtures of generally two modifications have always been formed.

The more thermodynamically stable triclinic modification has a melting point of from 99.5 to 100.5° C. and exhibits characteristic bands in the IR spectrum at 445, 568, 641, 769, 785 and 822 $cm^{-1}$.

As mentioned above, the prior art processes afford a second, less thermodynamically stable modification having a melting point of from 91.5 to 92.5° C. and characteristic bands in the IR spectrum at 428, 648, 704 and 805 $cm^{-1}$.

The process according to the invention also has the advantage that the preparation of the acid chloride II and also the bromination to the acid IIIa may be carried out in the same diluent as the Friedel-Crafts acylation. As shown in scheme 1 using the example of the preparation of 5-bromo-2',6-dimethyl-2,4',5',6'-tetramethoxybenzophenone (I'), (i) the bromination of 2-methoxy-6-methylbenzoic acid IV' to 5-bromo-2-methoxy-6-methylbenzoic acid IIIa', (ii) the subsequent conversion to the acid chloride II' and finally (iii) the Friedel-Crafts acylation to benzophenone I' can all be carried out in chlorobenzene.

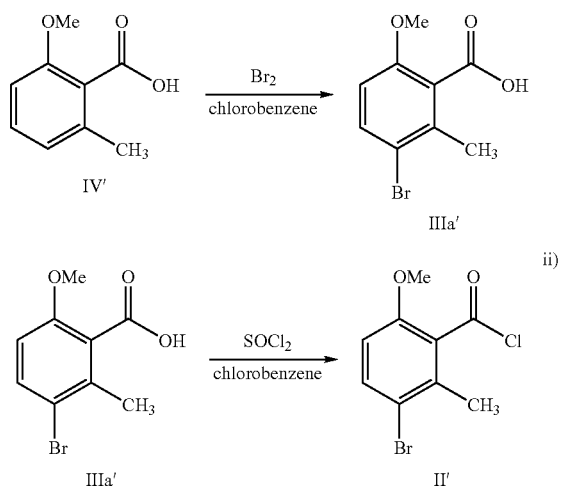

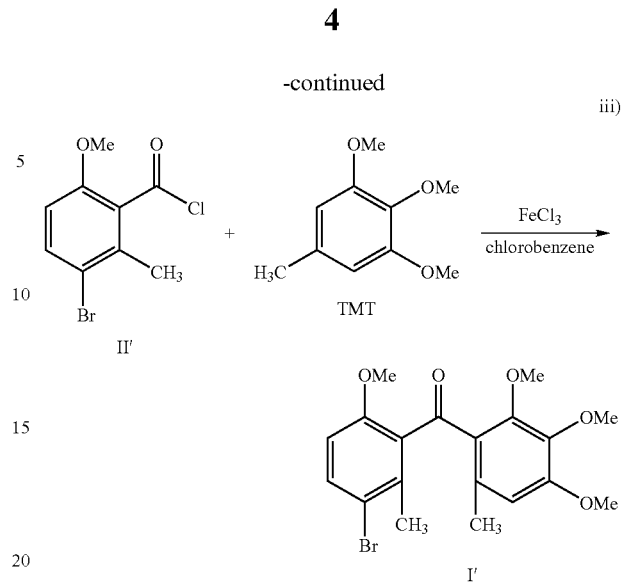

Depending on the metering sequence in the Friedel-Crafts stage, all three reaction steps can therefore be combined in a one-pot variant.

The relatively high boiling points of the diluent in the process according to the invention also allow the starting materials (bromine in the bromination step, thioinyl chloride (phosgene) in the acid chloride stage and 3,4,5-trimethoxytoluene in the Friedel-Crafts stage, each of which is preferably used in excess) to be distillatively removed and recycled back into the particular process (i to iii). When halogenated hydrocarbons such as benzotrichloride or chlorobenzene are used as diluents, the boiling point differences allow a diluent to be obtained by distillation in the Friedel-Crafts stage (iii) which is free of 3,4,5-trimethoxytoluene and can therefore be recycled directly into the bromination stage (i).

The formation of the acid chloride (stage ii) can be effected as described specifically in the literature. The chlorinating agent used is generally thionyl chloride or phosgene. The reaction temperature is typically from room temperature to 80° C.

The bromination (stage i) may be carried out as described in the literature. The reaction can either be carried out in the presence of, although preferably without, acid catalysis. The reaction temperature is generally from 0 to 80° C.

PROCESS EXAMPLES

Examples 1 to 7

General Process Procedure for Preparing 5-bromo-2',6-dimethyl-2,4',5',6'-tetramethoxybenzophenone (I') starting from 5-bromo-2-methoxy-6-methylbenzoyl chloride (II')

A solution of 1047 g (3.973 mol) of 5-bromo-2-methoxy-6-methyl-benzoyl chloride in 1715 g of chlorobenzene was admixed with 0.72 g (0.0044 mol) (examples 1 to 4 and 7) or 0.36 g (0.0022 mol) (example 5) or 0.18 g (0.0011 mol) (example 6) of anhydrous iron(III) chloride and metered into a solution of 868.7 g (4.768 mol) of 3,4,5-trimethoxytoluene in 467.8 g of chlorobenzene at the reaction temperature stated in the table over 4 h. Subsequently, the reaction mixture was stirred at the reaction temperature for a further 2 h. To remove the HCl formed, a constant nitrogen stream was passed through the reaction mixture during the metering and continued stirring time (the particular flow rate may be taken from the table). Subsequently, the chlorobenzene was distilled off at 80 mbar and temperatures of 80-105° C. Purity and yield of the crude product melt were determined by means of quantitative HPLC before crystallization (see table for results).

To crystallize the 5-bromo-2',6-dimethyl-2,4',5',6'-tetramethoxy-benzophenone (I'), 4900 g of methanol were initially charged at 50° C. and the melt at 105° C. was introduced. The crystallization was effected by cooling by means of a temperature ramp down to −5° C. The title compound was isolated by centrifugation, washed with methanol on the centrifuge and dried.

| Experiment | Mole percent of FeCl₃ | N₂ flow rate | Reaction temperature | Conversion after 6 h | Selectivity | Yield after dist. |
|---|---|---|---|---|---|---|
| 1 | 0.11 | 10 l/h | 80° C. | 76.7% | 99.3% | 97.4% |
| 2 | 0.11 | 10 l/h | 100° C. | 90.4% | 99.3% | 97.5% |
| 3 | 0.11 | 5 l/h | 120° C. | 96.0% | 98.9% | 98.3% |
| 4 | 0.11 | 10 l/h | 145° C. | 100.0% | 97.8% | 97.5% |
| 5 | 0.06 | 10 l/h | 145° C. | 99.5% | 99.4% | 99.0% |
| 6 | 0.03 | 10 l/h | 145° C. | 99.3% | 99.2% | 98.9% |
| Initial charging of the acid chloride | | | | | | |
| 7 | 0.11 | 10 l/h | 145° C. | 100.0% | 89.4% | 89.4% |

Example 8

Preparation of 5-bromo-2',6-dimethyl-2,4',5',6'-tetramethoxy-benzophenone (I') starting from 2-methoxy-6-methylbenzoic acid (IV')

(i) Preparation of 5-bromo-2-methoxy-6-methylbenzoic acid (IIIa')

700 g (4.212 mol) of 2-methoxy-6-methylbenzoic acid (IV') were suspended in 2343.5 g of chlorobenzene, and 707.2 g (4.423 mol) of elemental bromine were subsequently added dropwise within 3 h at a constant internal temperature of 15° C. Afterwards, the mixture was stirred at 35° C. for 2 h. Subsequently, 628.7 g of chlorobenzene were distilled off at an internal temperature of 77-82° C. and 200 mbar, and the excess bromine and HBr were likewise removed from the reaction vessel. After analysis of the bromine content, the brominous chlorobenzene distillate could be reused in the next batch without any discharge. The amount of bromine to be used there could be correspondingly reduced.

The composition of the crude mixture was determined by quantitative HPLC. 980.5 g (4.0 mol=95% yield) of a suspension of IIIa' in chlorobenzene were obtained. The selectivity of the bromination is high. The ratio of 5-bromo to 3-bromo compound is >500:1.

(ii) Preparation of 5-bromo-2-methoxy-6-methylbenzoyl chloride (II')

The suspension obtained under (i) was diluted by adding 754.8 g of chlorobenzene and cooled to a temperature of 50° C. 0.95 g (0.013 mol) of dimethylformamide was then added, and 528.8 g (4.445 mol) of thionyl chloride were subsequently metered in at an internal temperature of 50° C. within 1.5 h. Finally, stirring was continued at 50° C. for a further 1.5 h. Afterwards, 754.8 g of chlorobenzene were distilled off at an internal temperature of 83-90° C. at 200 mbar, and excess thionyl chloride and residual hydrochloric acid and sulfur dioxide were also removed from the reaction mixture. After analyzing the thionyl chloride content, the thionyl chloride-containing chlorobenzene distillate could be reused in the next batch without any discharge. The amount of thionyl chloride to be used there could be correspondingly reduced.

The product of value content of the distillation residue was determined by means of quantitative HPLC. 1047 g (3.973 mol=99.5% yield) of 5-bromo-2-methoxy-6-methylbenzoyl chloride were obtained as a solution in chlorobenzene.

iii) Preparation of 5-bromo-2',6-dimethyl-2,4',5',6'-tetramethoxybenzophenone (I')

The preparation was effected in a similar manner to examples 1 to 7, likewise in chlorobenzene. Comparable results were obtained with regard to yield and purity of the products formed.

We claim:
1. A process for preparing benzophenones of the formula I,

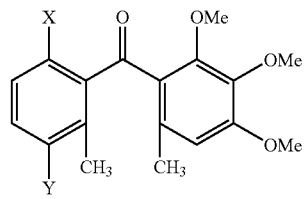

where X may be chlorine, hydroxyl, methoxy or $C_1C_6$-alkylcarbonyloxy, and Y may be chlorine or bromine, by reacting an acid chloride of the formula II

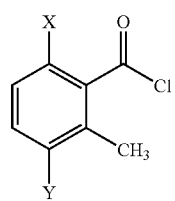

where X and Y are as defined above with 3,4,5-trimethoxytoluene, which comprises carrying out the reaction in the presence of
  a) an aromatic hydrocarbon selected from the group of: chlorobenzene, benzotrifluoride and nitrobenzene as a diluent and
  b) from 0.01 to 0.2 mol % of an iron catalyst, based on the acid chloride,
  c) at a temperature between 60° C. and the boiling point of the particular diluent.

2. A process as claimed in claim 1, wherein the diluent used is chlorobenzene.

3. A process as claimed in claim 1 or 2, wherein 3,4,5-trimethoxytoluene is initially charged, optionally in the particular diluent, and the acid chloride together with the iron catalyst is metered in, optionally in the particular diluent.

4. A process as claimed in claim 1, wherein the hydrochloric acid forming in the reaction is removed from the reaction mixture by stripping using an inert gas stream.

5. A process as claimed in claim 4, wherein the diluent is distilled off toward the end or during the course of the reaction, and the remaining product melt is crystallized in a $C_1$-$C_6$-alcohol.

6. A process as claimed in claim 1, wherein the acid chloride of the formula II is prepared by reacting an acid of the formula III

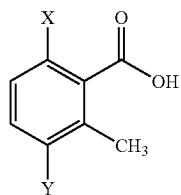

III where X and Y are each as defined above with thionyl chloride or phosgene, optionally in the presence of dimethylformamide, in the same diluent which is also used in the subsequent Friedel-Crafts stage.

7. A process as claimed in claim 6, wherein, after formation of the acid chloride II, at least a portion of the diluent is distilled off with excess thionyl chloride and recycled into the process.

8. A process as claimed in claim 6, wherein the acid of the formula IIIa

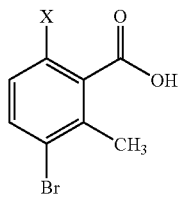

IIIa is prepared by brominating the compound IV

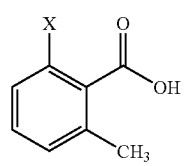

IV with elemental bromine in the same diluent which is also used in the two subsequent stages.

9. A process as claimed in claim 8, wherein at least a portion of the diluent and excess bromine is distilled off at the end of the bromination and recycled into the process.

10. A process as claimed in claim 1, wherein the amount of iron catalyst is 0.03 to 0.1 mol %, based upon the acid chloride.

11. A process as claimed in claim 1, wherein the amount of iron catalyst is less than 0.1 mol %, based upon the acid chloride.

12. A process as claimed in claim 1, wherein the diluent used is benzotrifluoride.

13. A process as claimed in claim 1, wherein the diluent used is nitrobenzene.

* * * * *